(12) United States Patent
Park et al.

(10) Patent No.: US 11,514,724 B2
(45) Date of Patent: Nov. 29, 2022

(54) BIOMETRIC DEVICE AND BIOMETRIC SYSTEM INCLUDING THE SAME

(71) Applicant: Electronics and Telecommunications Research Institute, Daejeon (KR)

(72) Inventors: Young Sam Park, Daejeon (KR); Seung Youl Kang, Daejeon (KR); Chul Woong Joo, Sejong-si (KR); Jae-Eun Pi, Sejong-si (KR)

(73) Assignee: Electronics and Telecommunications Research Institute, Daejeon (KR)

( * ) Notice: Subject to any disclaimer, the term of this patent is extended or adjusted under 35 U.S.C. 154(b) by 0 days.

(21) Appl. No.: 17/331,300

(22) Filed: May 26, 2021

(65) Prior Publication Data

US 2022/0036104 A1 Feb. 3, 2022

(30) Foreign Application Priority Data

Jul. 28, 2020 (KR) .................. 10-2020-0093845
Dec. 14, 2020 (KR) .................. 10-2020-0174649

(51) Int. Cl.
*G06K 9/00* (2022.01)
*G06V 40/60* (2022.01)
*G02F 1/1339* (2006.01)
*G02B 27/10* (2006.01)
*G02F 1/1343* (2006.01)
*G06V 40/13* (2022.01)

(52) U.S. Cl.
CPC ........... *G06V 40/67* (2022.01); *G02B 27/106* (2013.01); *G02F 1/1339* (2013.01); *G02F 1/134309* (2013.01); *G06V 40/1312* (2022.01); *G06V 40/1318* (2022.01)

(58) Field of Classification Search
CPC ............... G06V 40/67; G06V 40/1318; G06V 40/1312; G06V 40/1324; G02B 27/106; G02F 1/1339; G02F 1/134309
See application file for complete search history.

(56) References Cited

U.S. PATENT DOCUMENTS

| 10,211,596 | B2 | 2/2019 | Oh |
| 2014/0085641 | A1 | 3/2014 | Sohn et al. |
| 2017/0357841 | A1* | 12/2017 | Popovich ........... G06V 40/1324 |
| 2020/0050829 | A1 | 2/2020 | Akcasu |
| 2021/0124900 | A1 | 4/2021 | Kim et al. |

FOREIGN PATENT DOCUMENTS

| KR | 1020160106378 A | 9/2016 |
| KR | 1020200008964 A | 1/2020 |

* cited by examiner

*Primary Examiner* — Abdul-Samad A Adediran
(74) *Attorney, Agent, or Firm* — William Park & Associates Ltd.

(57) ABSTRACT

Disclosed are a biometric device and a biometric system including the same. The device includes a biogenic-synthesized film, a reflective layer disposed on one side of the biogenic-synthesized film, a light source disposed on the reflective layer to generate light, a beam splitter disposed between the light source and the reflective layer to provide the light to the reflective layer and another side of the biogenic-synthesized film, and a light switching layer disposed between the beam splitter and the reflective layer to switch the light provided to the reflective layer.

19 Claims, 8 Drawing Sheets

BIOMETRIC DEVICE AND BIOMETRIC SYSTEM INCLUDING THE SAME

CROSS-REFERENCE TO RELATED APPLICATIONS

This U.S. non-provisional patent application claims priority under 35 U.S.C. § 119 of Korean Patent Application Nos. 10-2020-0093845, filed on Jul. 28, 2020, and 10-2020-0174649, filed on Dec. 14, 2020, the entire contents of which are hereby incorporated by reference.

BACKGROUND

The present disclosure herein relates to a biometric system, and more particularly, to a biometric device and a biometric system including the same.

In general, a biometric technology is used to recognize individual biological characteristics and use the characteristics in a security system. Biometrics may be applied to, for example, fingerprint, voice, face, iris, palm lines, vein distribution, and the like. In particular, fingerprint recognition may be performed in response to a contact of a user's finger on a cover glass embedded in a mobile terminal such as a cell phone. A biometric system may recognize a user's fingerprint to unlock a screen if the recognized fingerprint matches a previously stored fingerprint of the user, otherwise the biometric system may maintain the state of a locked screen.

SUMMARY

The present disclosure provides a biometric device capable of presenting an examination position of a subject.

The present disclosure also provides a biometric device capable of contactless recognizing a subject and a biometric system including the same.

An embodiment of the inventive concept provides a biometric device including a biogenic-synthesized film; a first reflective layer disposed on one side of the biogenic-synthesized film; a light source disposed on the first reflective layer to generate light; a first beam splitter disposed between the light source and the first reflective layer to provide the light to the first reflective layer and another side of the biogenic-synthesized film; and a first light switching layer disposed between the first beam splitter and the first reflective layer to switch the light provided to the first reflective layer.

In an embodiment, the first light switching layer may include a liquid crystal panel.

In an embodiment, the first light switching layer may include: a lower substrate; a first lower electrode on the lower substrate; a liquid crystal layer on the first lower electrode; a first upper electrode on the liquid crystal layer; and an upper substrate on the first upper electrode.

In an embodiment, the first light switching layer may further include a sealing layer provided on edges of the first lower electrode and the first upper electrode and surrounding the liquid crystal layer.

In an embodiment, the biometric device may further include a light refraction layer disposed between the first beam splitter and the first light switching layer.

In an embodiment, the light refraction layer may further include: a second lower electrode; a refractive index changing layer on the second lower electrode; and a second upper electrode on the refractive index clanging layer.

In an embodiment, the biometric device may further include: a light absorption layer disposed on the light source to absorb light on the light source; and a collimator disposed between the light absorption layer and the light source.

In an embodiment, the biometric device may further include: a second reflective layer provided on the light source and reflecting the light to the light source or the biogenic-synthesized film; a second beam splitter disposed between the second reflective layer and the light source to provide the light to the second reflective layer or the biogenic-synthesized film; and a second light switching layer disposed between the second beam splitter and the light source to switch the light provided on the light source.

In an embodiment, the second light switching layer may be operated in an opposite manner to that of the first light switching layer.

In an embodiment, the biometric device may further include: a first interlayer insulation layer disposed between the first reflective layer and the biogenic-synthesized film; a second interlayer insulation layer disposed between the second reflective layer and the second beam splitter; and a third light switching layer disposed on sidewalls of the second beam splitter, the second interlayer insulation layer, and the second reflective layer.

In an embodiment of the inventive concept, a biometric system includes: a substrate; a biometric device disposed on one side of the substrate; and a sensing device disposed on another side of the substrate, wherein the biometric device includes: a biogenic-synthesized film on the substrate; a first reflective layer disposed on one side of the biogenic-synthesized film; a first light source disposed on the first reflective layer to generate first light; a first beam splitter disposed between the first light source and the first reflective layer to provide the first light to the first reflective layer and the other side of the biogenic-synthesized film; and a light switching layer disposed between the first beam splitter and the first reflective layer to switch the first light provided to the first reflective layer.

In an embodiment, the substrate may include a flexible substrate.

In an embodiment, the flexible substrate may include polyimide or polyethylene naphthalene.

In an embodiment, the sensing device may include: a second light source configured to generate second light; and a light sensor disposed adjacent to the second light source and receiving the second light.

In an embodiment, each of the first light source and the second light source may include a light emitting device.

In an embodiment, the biometric device and the sensing device may be alternately disposed in a first direction and in a second direction intersecting the first direction.

In an embodiment, the biometric system may further include a transparent cover connected to an edge of the substrate and covering the biometric device and the sensing device.

In an embodiment, the biometric device may be provided in plurality, wherein the plurality of biometric devices may be disposed on two sides of the sensing device.

In an embodiment, the substrate may be concavely bent so that the plurality of biometric devices come closer to each other.

BRIEF DESCRIPTION OF THE FIGURES

The accompanying drawings are included to provide a further understanding of the inventive concept, and are incorporated in and constitute a part of this specification.

The drawings illustrate embodiments of the inventive concept and, together with the description, serve to explain principles of the inventive concept. In the drawings.

DETAILED DESCRIPTION

Figure 1:
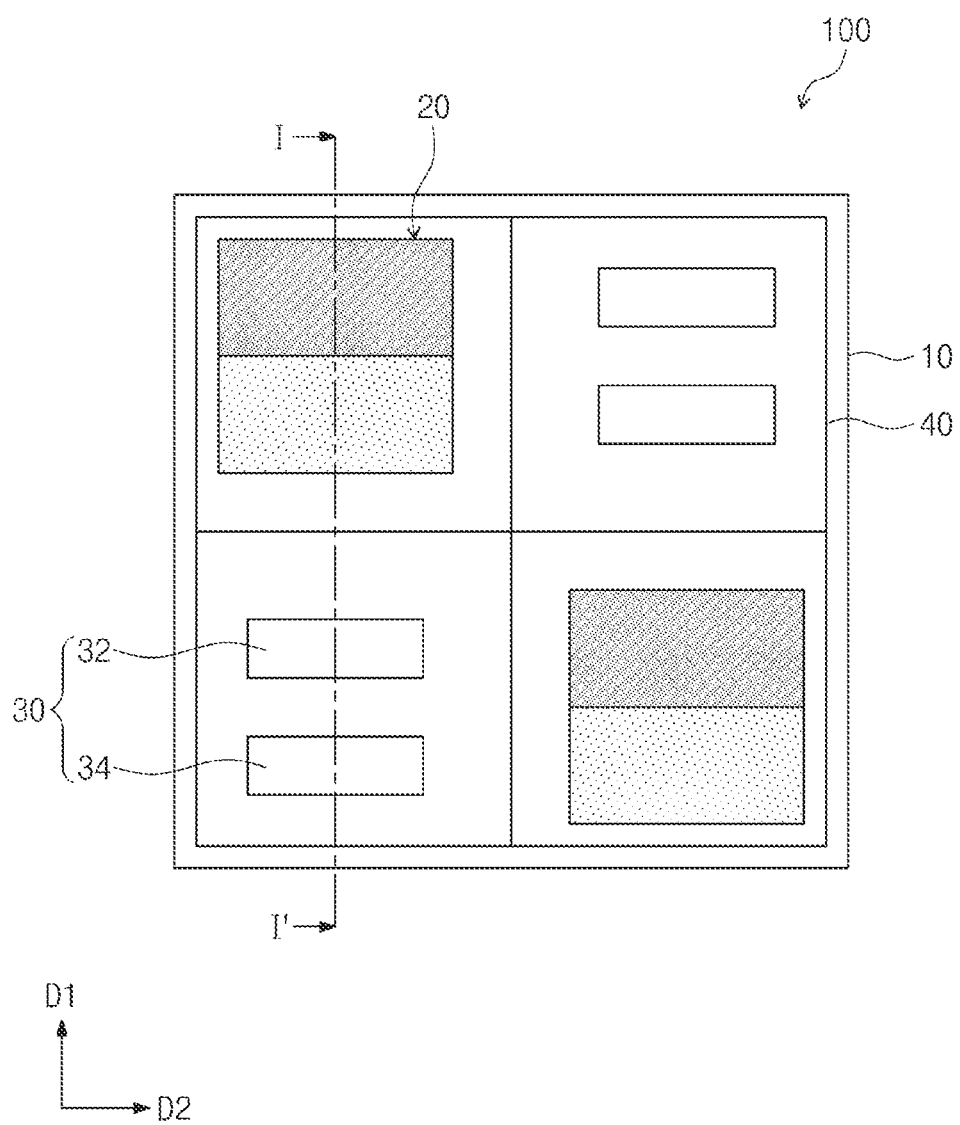
FIG. 1 illustrates an example of a biometric system according to an embodiment of the inventive concept.

Hereinafter, embodiments of the inventive concept will be described in detail with reference to the accompanying drawings. Advantages and features of the inventive concept, and implementation methods thereof will be clarified through following embodiments described with reference to the accompanying drawings. Therefore, the inventive concept may be embodied in different forms and should not be construed as limited to the embodiments set forth herein. Rather, these embodiments are provided so that this disclosure will be thorough and complete, and will fully convey the scope of the inventive concept to those skilled in the art, and the inventive concept is only defined by the scope of the claims. Like reference numerals refer to like elements throughout.

The terminology used herein is not for delimiting the embodiments of the inventive concept but for describing the embodiments. The terms of a singular form may include plural forms unless otherwise specified. It will be further understood that the terms "includes", "including", "comprises", and/or "comprising", when used in this description, specify the presence of stated elements, operations, and/or components, but do not preclude the presence or addition of one or more other elements, operations, and/or components. Furthermore, reference numerals, which are presented in the order of description, are provided according to the embodiments and are thus not necessarily limited to the order.

The embodiments of the inventive concept will be described with reference to exemplary cross-sectional views and/or planar views. In the drawings, the substrates, biometric films, and light refraction layers are exaggerated for clarity of illustration. Therefore, the forms of the exemplary drawings may be changed due to a manufacturing technology and/or error tolerance. Therefore, the embodiments of the inventive concept may involve changes of shapes depending on a manufacturing process, without being limited to the illustrated specific forms.

Figure 2:
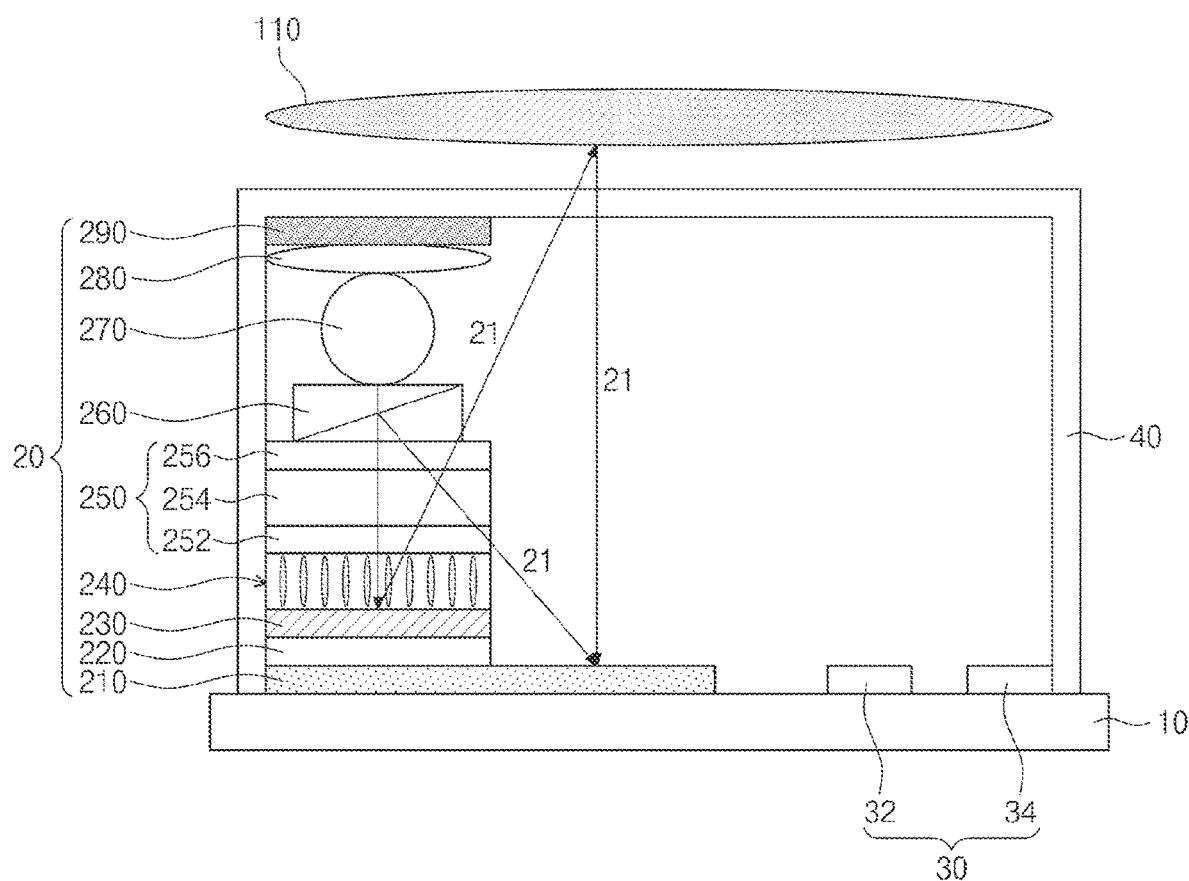
FIG. 2 is a cross-sectional view of the system taken along line of FIG. 1.

FIG. 1 illustrates an example of a biometric system 100 according to an embodiment of the inventive concept. FIG. 2 is a cross-sectional view of the system taken along line I-I' of FIG. 1.

Referring to FIGS. 1 and 2, the biometric system 100 of an embodiment of the inventive concept may include a substrate 10, biometric devices 20, sensing devices 30, and a transparent cover 40. The substrate 10 may include a flexible substrate. For example, the substrate 10 may include polyimide and polyethylenenaphthalene. The biometric devices 20 and the sensing devices 30 may be provided on the substrate 10. The biometric devices 20 and the sensing devices 30 may be alternately disposed in a first direction D1 and in a second direction D2. The transparent cover 40 may be connected to an edge of the substrate 10 and may cover the biometric devices 20 and the sensing devices 30. The transparent cover 40 may include transparent plastics or transparent quartz, but an embodiment of the inventive concept is not limited thereto.

Referring to FIG. 2, the biometric device 20 may be provided on one side of the substrate 10. The biometric device 20 may write and/or memorize an image (e.g., biometric information) of a reference living body 110 using a holographic principle related to a first light 21. The reference living body 110 may be provided above the transparent cover 40 without contacting the transparent cover 40. That is, the image of the living body 110 may be contactlessly written and/or memorized. For example, the biometric device 20 may include a biogenic-synthesized film 210, a first interlayer insulation layer 220, a first reflective layer 230, a first light switching layer 240, a light refraction layer 250, a first beam splitter 260, a first light source 270, a collimator 280, and a light absorption layer 290.

Figure 4:
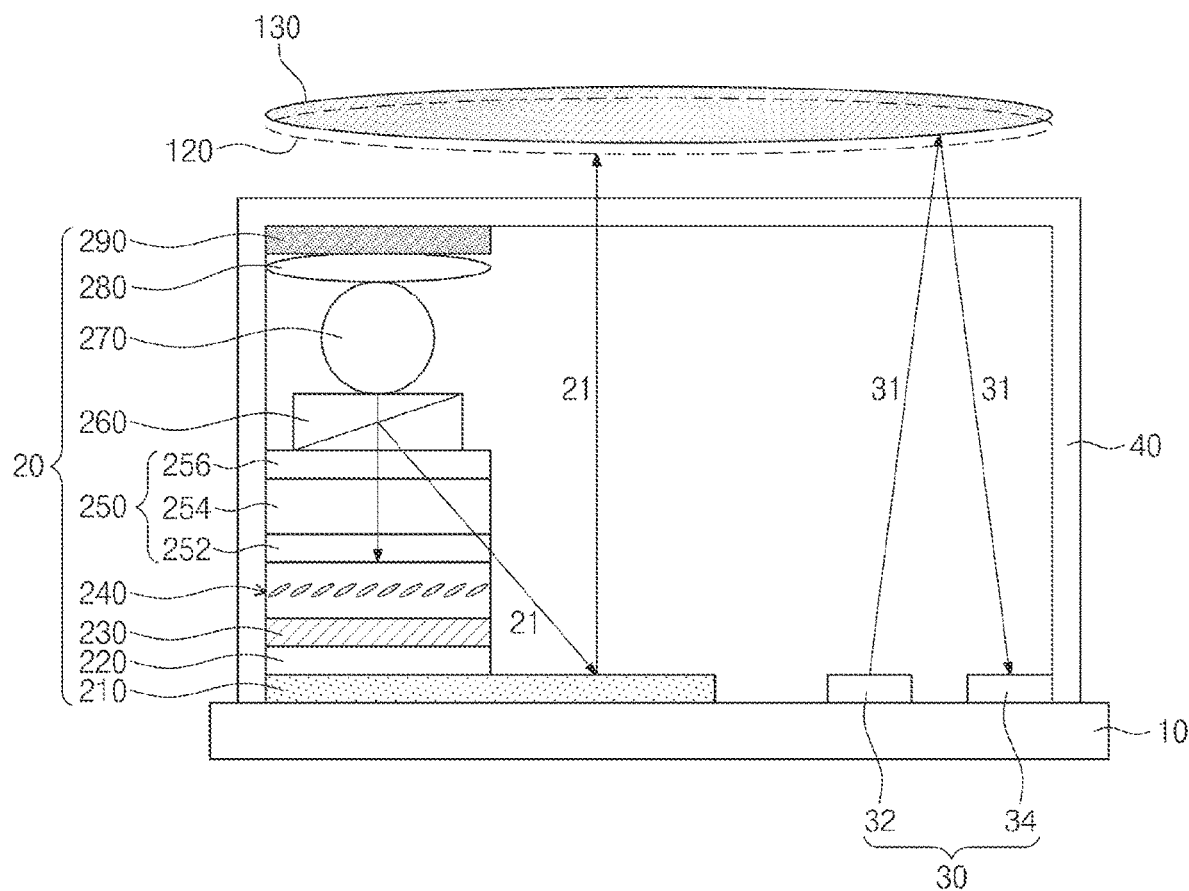
FIG. 4 is a cross-sectional view illustrating a virtual living body displayed using the first light of FIG. 2.

The biogenic-synthesized film 210 may be provided on the substrate 10. When the first light 21 forms an image on the biogenic-synthesized film 210 on the basis of a holographic principle, the biogenic-synthesized film 210 may write and/or memorize the image of the reference living body 110. The reference living body 110 may include a human finger. The reference living body 110 may be the same as or different from a subject 130 (FIG. 4). For example, the biogenic-synthesized film 210 may include photopolymer, photoresist, silver halide emulsion, dichromated gelatin, photographic emulsion, photothermoplastic, polycarbonate (PC), polypropylene (PP), polyethylene terephthalate (PET), or triacetylose (TAC).

The first interlayer insulation layer 220 may be disposed on one side of the biogenic-synthesized film 210. The first interlayer insulation layer 220 may be disposed between the biogenic-synthesized film 210 and the first reflective layer 230 to provide a planar surface to the first reflective layer 230. For example, the first interlayer insulation layer 220 may include a dielectric of silicon oxide or silicon nitride.

The first reflective layer 230 may be disposed on the first interlayer insulation layer 220. The first reflective layer 230 may reflect the first light 21 to the reference living body 110. For example, the first reflective layer 230 may include metals such as Al, Ag, or Cu, but an embodiment of the inventive concept is not limited thereto.

The first light switching layer 240 may be disposed on the first reflective layer 230. The first light switching layer 240 may switch the first light 21. For example, the first light switching layer 240 may transmit the first light 21 to the first reflective layer 230 or may block the first light 21.

Figure 3:
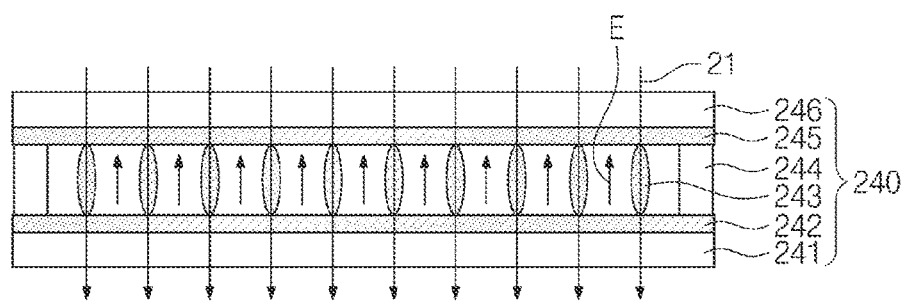
FIG. 3 is a cross-sectional view illustrating an example of the light switching layer of FIG. 2.

FIG. 3 illustrates an example of the first light switching layer 240 of FIG. 2.

Referring to FIG. 3, the first light switching layer 240 may include a liquid crystal panel. The first light switching layer 240 may transmit the first light 21 in a direction parallel to an electric field E. For example, the first light switching layer 240 may include a lower substrate 241, a first lower electrode 242, a liquid crystal layer 243, a sealing layer 244, a first upper electrode 245, and an upper substrate 246. The lower substrate 241 may include a transparent substrate. For example, the lower substrate 241 may include a glass or transparent plastic substrate. The first lower electrode 242 may be provided on the lower substrate 241. The first lower electrode 242 may include a transparent electrode such as an indium tin oxide (ITO) electrode. The liquid crystal layer 243 may be provided on the first lower electrode 242. When the electric field E is induced between the first lower electrode 242 and the first upper electrode 245, the liquid crystal layer 243 may be disposed along the electric field E and may transmit the first light 21. For example, the liquid crystal layer 243 may include nematic liquid crystals. The sealing layer 244 may be provided at an edge of the first lower electrode 242. The sealing layer 244 may surround the liquid crystal layer 243 and may seal the liquid crystal layer 243 between the lower substrate 241 and the upper substrate 246. For example, the sealing layer 244 may include an epoxy adhesive, but an embodiment of the inventive concept is not limited thereto. The first upper electrode 245 may be provided on the liquid crystal layer 243 and the sealing layer 244. For example, the first upper electrode 245 may include a transparent electrode such as an ITO electrode. The upper substrate 246 may be provided on the first upper electrode 245. The upper substrate 246 may include a glass or transparent plastic substrate, but an embodiment of the inventive concept is not limited thereto.

Referring back to FIG. 2, the light refraction layer 250 may be provided on the first light switching layer 240. The light refraction layer 250 may transmit the first light 21. When the first light 21 is provided from the first beam splitter 260, the light refraction layer 250 may refract a portion of the first light 21 to the first light switching layer 240, and may refract another portion of the first light 21 to another side of the biogenic-synthesized film 210. For example, the light refraction layer 250 may include a second lower electrode 252, a refractive index changing layer 254, and a second upper electrode 256. The second lower electrode 252 may be provided on the first light switching layer 240. The second lower electrode 252 may heat the refractive index changing layer 254 to change a refractive index of the refractive index changing layer 254. For example, the second lower electrode 252 may include a metal oxide such as $TiO_2$, ZnO, and ITO. The refractive index changing layer 254 may be provided on the second lower electrode 252. The refractive index changing layer 254 may change the refractive index to scan the other side of the biogenic-synthesized film 210 with the first light 21. For example, the refractive index changing layer 254 may include silica. The second upper electrode 256 may be provided on the refractive index changing layer 254. The second upper electrode 256 may heat the refractive index changing layer 254 to accelerate changing of the refractive index of the refractive index changing layer 254. For example, the second upper electrode 256 may include a metal oxide such as $TiO_2$, ZnO, and ITO.

The first beam splitter 260 may be provided on the light refraction layer 250. The first beam splitter 260 may divide the first light 21 to provide a portion of the first light 21 to the first reflective layer 230 and provide another portion of the first light 21 to the other side of the biogenic-synthesized film 210. For example, the first beam splitter 260 may include a birefringent material such as calcite, but an embodiment of the inventive concept is not limited thereto.

The first light source 270 may be provided on the first beam splitter 260. The first light source 270 may generate the first light 21. For example, the first light source 270 may include a light emitting device (LED).

Although not illustrated, an additional collimator may be provided between the first light source 270 and the first beam splitter 260. The additional collimator may collimate the first light 21 to improve precision of division of the first light 21 by the first beam splitter 260.

The collimator 280 may be provided on the first light source 270. The first light 21 is light required for writing and/or memorizing an image of a reference living body using a holographic principle. Light is radiated from the first light source 270 in all directions, and the collimator 280 may collimate light other than the first light 21, i.e., undesired light, to the light absorption layer 290. For example, the collimator 280 may include a convex lens. The light absorption layer 290 may be provided on the collimator 280. The light absorption layer 290 may absorb undesired light, thereby preventing interference with the first light 21. For example, the light absorption layer 290 may include metal such as chrome (Cr). Alternatively, the light absorption layer 290 may include graphene and a carbon nanotube array.

Figure 5:
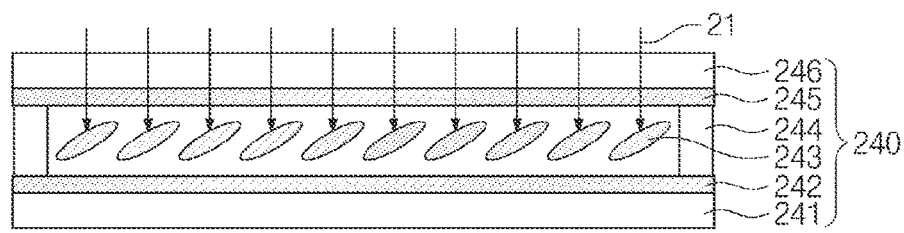
FIG. 5 is a cross-sectional view illustrating an example of the light switching layer of FIG. 4.

FIG. 4 illustrates a virtual living body 120 displayed using the first light 21 of FIG. 2. FIG. 5 illustrates an example of the first light switching layer 240 of FIG. 4.

Referring to FIGS. 4 and 5, when the first light switching layer 240 blocks a portion of the first light 21, the first beam splitter 260 may reflect another portion of the first light 21 to the biogenic-synthesized film 210 to display the virtual living body 120 above the transparent cover 40 on the other side of the biogenic-synthesized film 210. The virtual living body 120 may not contact the transparent cover 40. The virtual living body 120 may notify an examinee (not shown) of an examination position of the subject 130. The examinee may provide the subject 130 within the virtual living body 120 on the basis of the virtual living body 120. The subject 130 may overlap the virtual living body 120. The subject 130 may be contactlessly provided on the transparent cover 40. That is, the biometric system 100 may contactlessly certificate the subject 130. For example, the subject 130 may include a finger. When an electric field generated between the first lower electrode 242 and the first upper electrode 245 is removed, the liquid crystal layer 243 of the first light switching layer 240 may block a portion of the first light 21 to display the virtual living body 120 so as to present the examination position of the subject 130.

Referring to FIGS. 2 and 4, the sensing device 30 may be provided on the other side of the substrate 10. The sensing device 30 may sense the subject 130 by providing a second light 31 to the subject 130. A control unit (not show may obtain an image of the subject 130 using a sensing signal of the sensing device 30, and may certificate the subject 130. For example, the sensing device 30 may include a second light source 32 and a light detector 34.

The second light source 32 may be provided between the biometric device 20 and the light detector 34. The second light source 32 may generate and provide the second light 31 to the subject 130. The second light 31 may have a wavelength different from a wavelength of the first light 21. The second light source 32 may include a light emitting device (LED).

The light detector 34 may be disposed adjacent to the second light source 32. The light detector 34 may receive the second light 31 to generate the image of the subject 130. The light detector 34 may include a CMOS device or CCD. Alternatively, the light detector 34 may include a photodiode or phototransistor, but an embodiment of the inventive concept is not limited thereto. The control unit (not shown) may certificate the subject 130 using the image of the light detector 34. When the subject 130 is the same as the reference living body 110, the control unit may determine that the subject 130 is normal. When the subject 130 is different from the reference living body 110, the control unit may determine that the subject 130 has an error.

Figure 6:
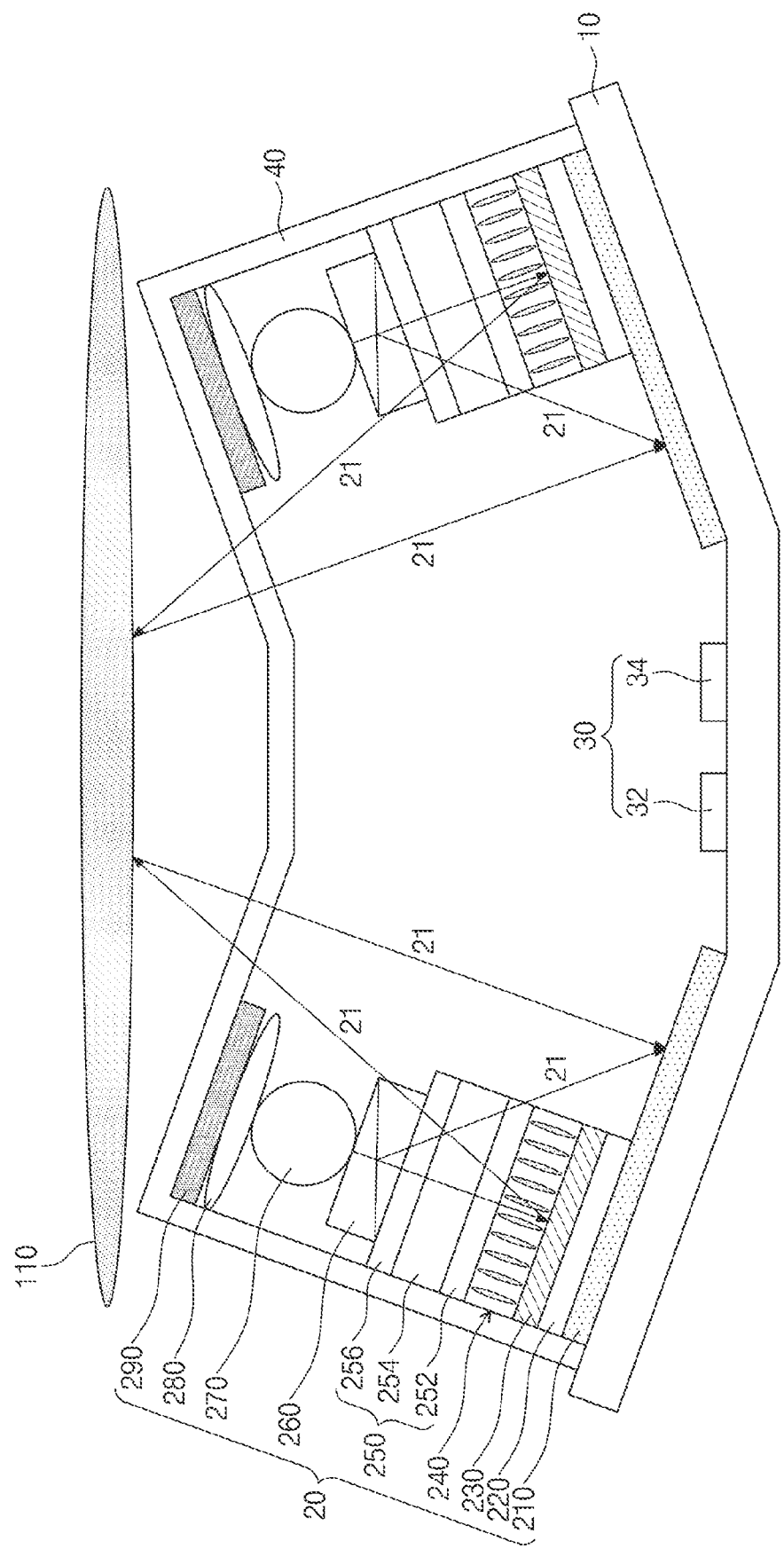
FIG. 6 is a cross-sectional view illustrating an example of the biometric devices of FIG. 2.

FIG. 6 illustrates an example of the biometric devices 20 of FIG. 2.

Referring to FIG. 6, the plurality of biometric devices 20 may be disposed on two sides of the sensing device 30, and may concentrate the first light 21 on the reference living body 110 disposed on the sensing device 30. The substrate 10 may be concavely bent so that the biometric devices 20 come closer to each other. When the substrate 10 is bent, the transparent cover 40 may be bent in the same shape as the substrate 10. The first light 21 may be provided to the biogenic-synthesized films 210 after being reflected from the reference living body 110 so that the image of the reference living body 110 may be written. The plurality of biometric devices 20 may write the image of the reference living body 110 having a large area on the biogenic-synthesized films 210.

Although not illustrated, the biometric devices 20 may concentrate the first light 21 to a region above the sensing device 30 so as to clearly display the virtual living body 120.

Figure 7:
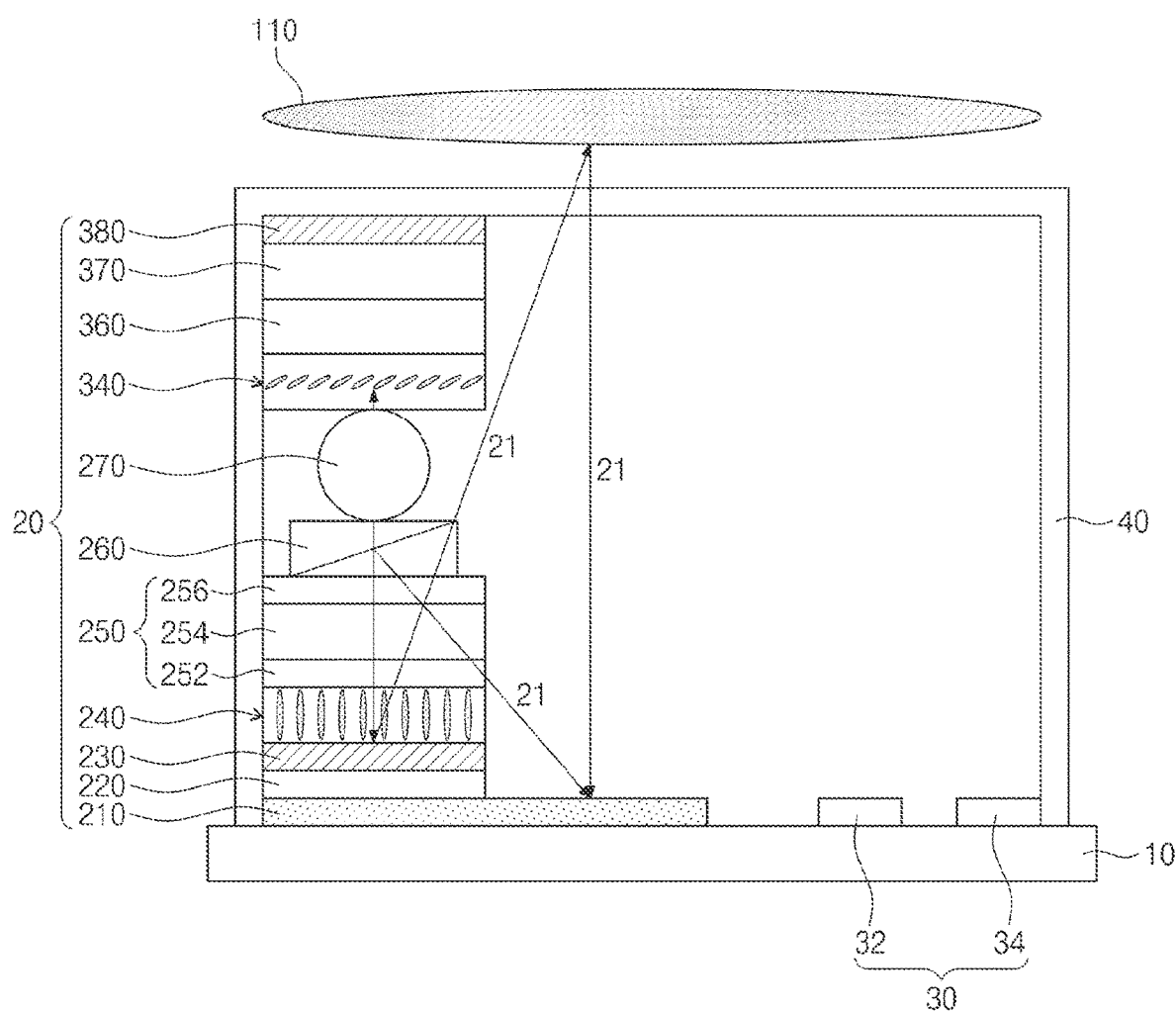
FIGS. 7 and 8 are cross-sectional views illustrating an example of the biometric device of FIG. 8.
Figure 8:
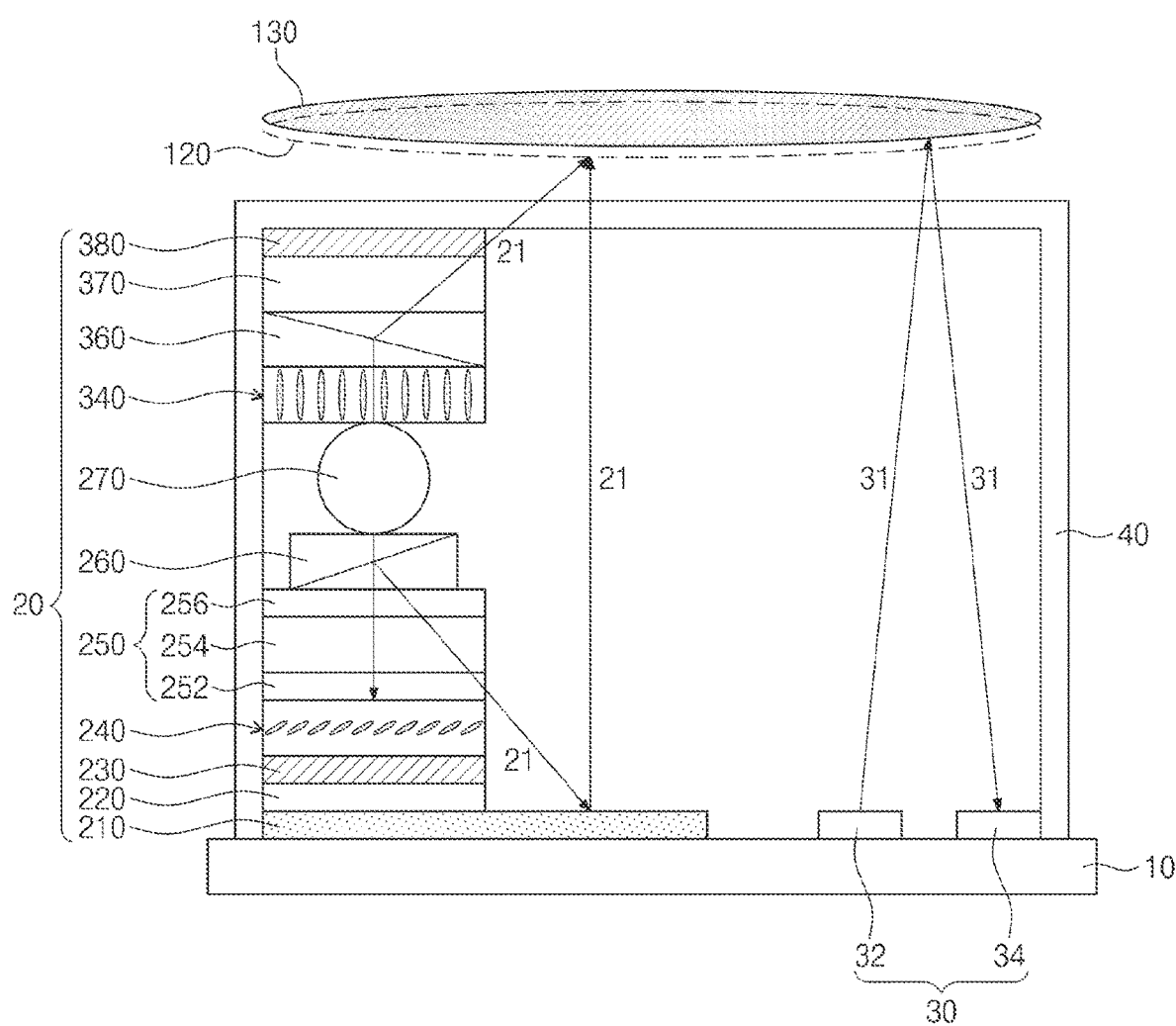

FIGS. 7 and 8 illustrate an example of the biometric device 20 of FIG. 1.

Referring to FIGS. 7 and 8, the biometric device 20 may further include a second light switching layer 340, a second beam splitter 360, a second interlayer insulation layer 370, and a second reflective layer 380. The collimator 280 and the light absorption layer 290 of FIG. 2 may be replaced with the second light switching layer 340, the second beam splitter 360, the second interlayer insulation layer 370 and the second reflective layer 380.

The second light switching layer 340 may be provided on the first light source 270. The second light switching layer 340 may control the first light 21 on the first light source 270. The second light switching layer 340 may be configured in the same manner as the first light switching layer 240 of FIGS. 3 and 5. The second light switching layer 340 may be operated in an opposite manner to that of the first light switching layer 240. The first light switching layer 240 and the second light switching layer 340 may be operated as described below.

Referring to FIG. 7, when the second light switching layer 340 blocks the first light 21 on the first light source 270, the first light switching layer 240 may transmit the first light 21 under the first light source 270 so as to write and/or memorize the image of the reference living body 110 on the biogenic-synthesized film 210 using a holographic method.

Referring to FIG. 8. When the first light switching layer 240 blocks the first light 21 under the first light source 270, the second light switching layer 340 may transmit the first light 21 on the first light source 270 to image the transmitted first light 21 with the first light 21 reflected from the biogenic-synthesized film 210 to thereby display the virtual living body 120 above the transparent cover 40 using a holographic method. The virtual living body 120 may be displayed in air above the transparent cover 40.

The second beam splitter 360 may be provided on the second light switching layer 340. The second beam splitter 360 may reflect a portion of the first light 21 to a region above the transparent cover 40 outside the second reflective layer 380, and may transmit a remaining portion of the first light 21 to the second interlayer insulation layer 370.

The second interlayer insulation layer 370 may be provided on the second beam splitter 360. The second interlayer insulation layer 370 may transmit the first light 21. The second interlayer insulation layer 370 may include a dielectric such as silicon oxide. Alternatively, the second interlayer insulation layer 370 may include a transparent polymer, but an embodiment of the inventive concept is not limited thereto.

The second reflective layer 380 may be provided on the second interlayer insulation layer 370. The second reflective layer 380 may reflect the second light 31 to the first light source 270. Alternatively, the second reflective layer 380 may absorb the second light 31.

The biogenic-synthesized film 210, the first interlayer insulation layer 220, the first reflective layer 230, the first light switching layer 240, the light refraction layer 250, and the first beam splitter 260 may be configured in the same manner as illustrated in FIGS. 2 and 4.

Figure 9:
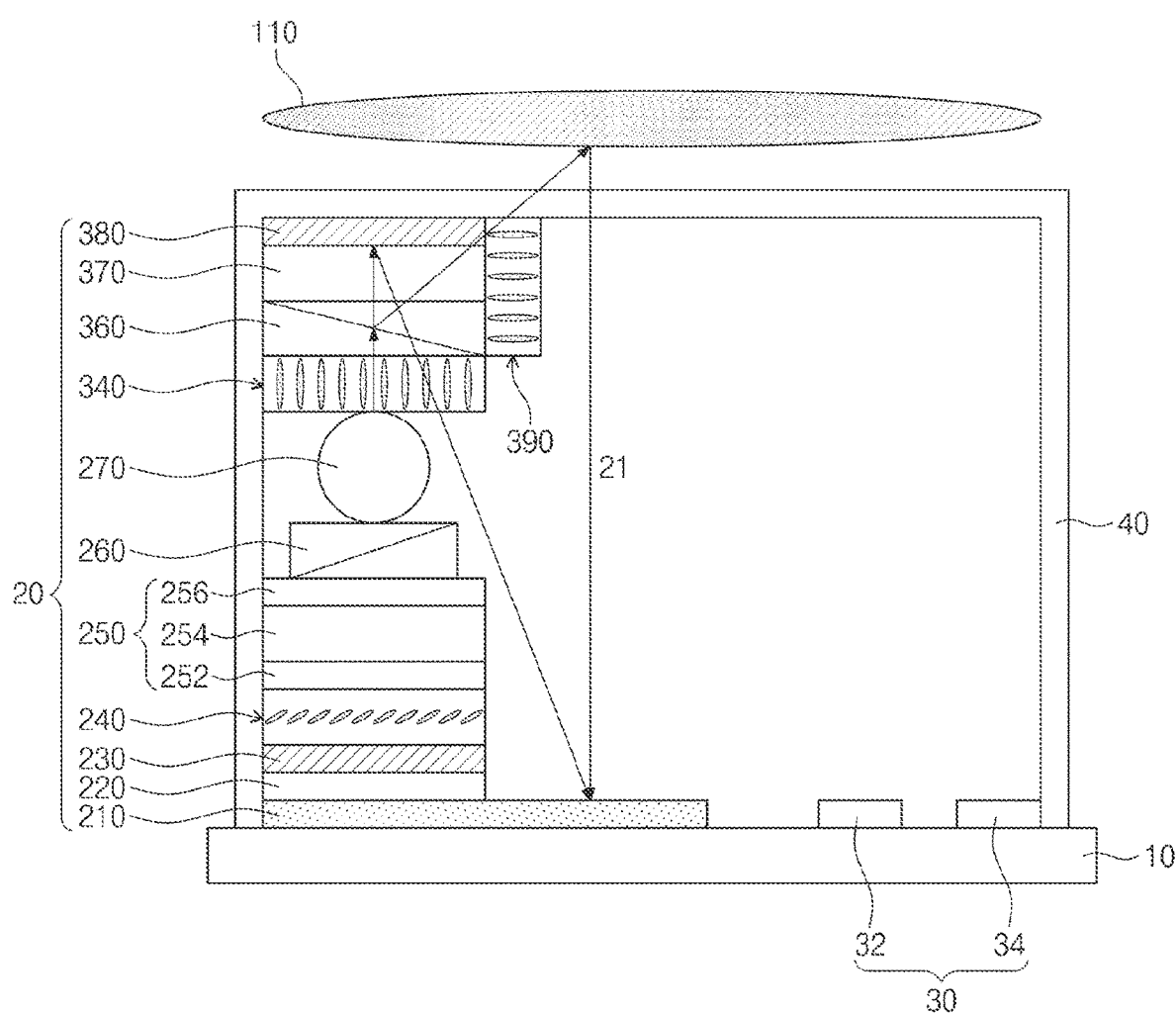
FIGS. 9 and 10 are cross-sectional views illustrating an example of the biometric device of FIG. 1.
Figure 10:
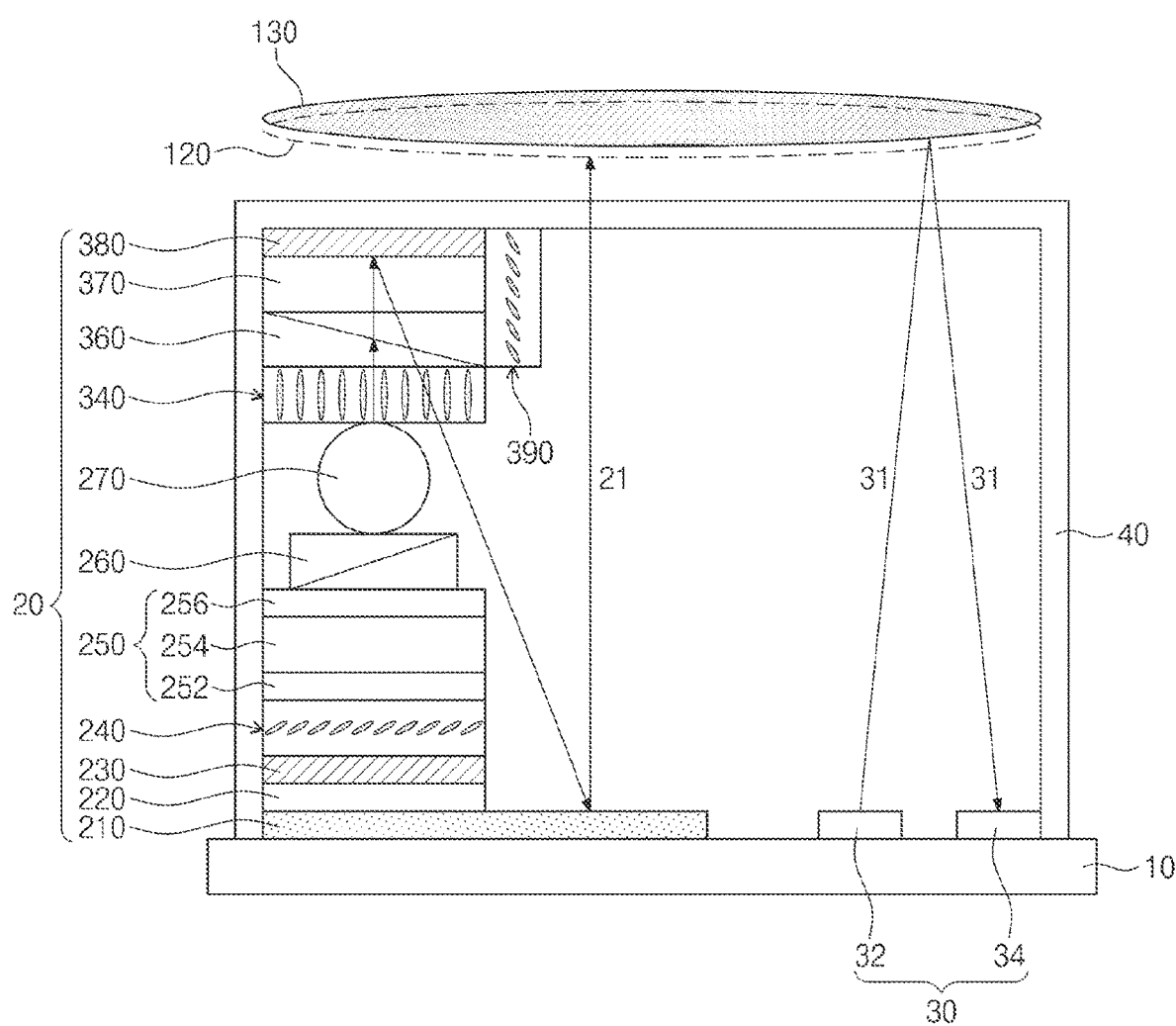

FIGS. 9 and 10 illustrate an example of the biometric device 20 of FIG. 1.

Referring to FIGS. 9 and 10, the biometric device 20 may further include a third light switching layer 390. The third light switching layer 390 may be provided on sidewalk of one sides of the second beam splitter 360, the second interlayer insulation layer 370, and the second reflective layer 380. The third light switching layer 390 may switch light that deviates from the second reflective layer 380 among the first light 21 on the first light source 270. That is, the third light switching layer 390 may pass the light that deviates from the second reflective layer 380 so as to direct the light towards the reference living body 110 as illustrated in FIG. 9, or may block the light that deviates from the second reflective layer 380 as illustrated in FIG. 10. In FIGS. 9 and 10, the light refraction layer 250 may function as an absorption layer to absorb the first light 21 under the first light source 270. In the case where the light refraction layer 250 absorbs the first light 21 under the first light source 270, the first light source 270, the second light switching layer 340, the second beam splitter 360, the second interlayer insulation layer 370, the second reflective layer 380, and the third switching layer 390 may use the first light 21 to write the image of the reference living body 110 as illustrated in FIG. 9 and display the virtual living body 120 as illustrated in FIG. 10.

Referring to FIG. 9, the second light switching layer 340 may transmit the first light 21 to write and/or memorize the image of the reference living body 110 on the biogenic-synthesized film 210 using a holographic method. The second beam splitter 360 may transmit a portion (e.g., reference light) of the first light 21, and may reflect a remaining portion (e.g., object light) of the first light 21. The portion (e.g., reference light) of the first light 21 may travel towards the biogenic-synthesized film 210 after affixing at the second reflective layer 380, and the remaining portion (e.g., object light) of the first light 21 may travel towards the biogenic-synthesized film 210 after arriving at the reference living body 110 so as to write the image of the reference living body 110 on the biogenic-synthesized film 210. The third light switching layer 390 may transmit the remaining portion (e.g., object light) of the first light 21 so that the remaining portion of the first light 21 may travel from the second beam splitter 360 to the reference living body 110.

Referring to FIG. 10, the third light switching layer 390 may block the remaining portion e.g., object light) of the first light 21 so as to display the image of the reference living body 110 as the virtual living body 120.

The second beam splitter 360 may allow the portion (e.g., reference light) of the first light 21 to arrive at the biogenic-synthesized film 210 after arriving at the second reflective layer 380 so that the virtual living body 120 may be displayed in air.

The first interlayer insulation layer 220, the first reflective layer 230, the first light switching layer 240, and the first beam splitter 260 may be configured in the same manner as illustrated in FIGS. 7 and 8.

As described above, a biometric device according to an embodiment of the inventive concept may write an image of a reference living body on a biogenic-synthesized film using a light switching layer and may display a virtual living body on the biogenic-synthesized film so as to present an examination position of a subject. A biometric system including a biometric device may contactlessly recognize a subject using a sensing device adjacent to the biometric device.

Although the embodiments of the present invention have been described, it is understood that the present invention should not be limited to these embodiments but various changes and modifications can be made by one ordinary skilled in the art within the spirit and scope of the present invention as hereinafter claimed.

What is claimed is:

1. A biometric device comprising:
a biogenic-synthesized film;
a first reflective layer disposed on one side of the biogenic-synthesized film;
a light source disposed on the first reflective layer to generate light;
a first beam splitter disposed between the light source and the first reflective layer to provide the light to the first reflective layer and another side of the biogenic-synthesized film; and
a first light switching layer disposed between the first beam splitter and the first reflective layer to switch the light provided to the first reflective layer.

2. The biometric device of claim 1,
wherein the first light switching layer comprises a liquid crystal panel.

3. The biometric device of claim 1, wherein the first light switching layer comprises:
a lower substrate;
a first lower electrode on the lower substrate;
a liquid crystal layer on the first lower electrode;
a first upper electrode on the liquid crystal layer; and
an upper substrate on the first upper electrode.

4. The biometric device of claim 3, wherein the first light switching layer further comprises a sealing layer provided on edges of the first lower electrode and the first upper electrode and surrounding the liquid crystal layer.

5. The biometric device of claim 1, further comprising a light refraction layer disposed between the first beam splitter and the first light switching layer.

6. The biometric device of claim 5, wherein the light refraction layer comprises:
a second lower electrode;
a refractive index changing layer on the second lower electrode; and
a second upper electrode on the refractive index changing layer.

7. The biometric device of claim 1, further comprising:
a light absorption layer disposed on the light source to absorb light on the light source; and
a collimator disposed between the light absorption layer and the light source.

8. The biometric device of claim 1, further comprising:
a second reflective layer provided on the light source and reflecting the light to the light source or the biogenic-synthesized film;
a second beam splitter disposed between the second reflective layer and the light source to provide the light to the second reflective layer or the biogenic-synthesized film; and
a second light switching layer disposed between the second beam splitter and the light source to switch the light provided on the light source.

9. The biometric device of claim 8,
wherein the second light switching layer is operated in an opposite manner to that of the first light switching layer.

10. The biometric device of claim 8, further comprising:
a first interlayer insulation layer disposed between the first reflective layer and the biogenic-synthesized film;
a second interlayer insulation layer disposed between the second reflective layer and the second beam splitter; and
a third light switching layer disposed on sidewalls of the second beam splitter, the second interlayer insulation layer, and the second reflective layer.

11. A biometric system comprising:
a substrate;
a biometric device disposed on one side of the substrate; and
a sensing device disposed on another side of the substrate,
wherein the biometric device comprises:
a biogenic-synthesized film on the substrate;
a first reflective layer disposed on one side of the biogenic-synthesized film;
a first light source disposed on the first reflective layer to generate first light;
a first beam splitter disposed between the first light source and the first reflective layer to provide the first light to the first reflective layer and another side of the biogenic-synthesized film; and
a light switching layer disposed between the first beam splitter and the first reflective layer to switch the first light provided to the first reflective layer.

12. The biometric system of claim 11, wherein the substrate comprises a flexible substrate.

13. The biometric system of claim 12, wherein the flexible substrate comprises polyimide or polyethylene naphthalene.

14. The biometric system of claim 11, wherein the sensing device comprises:
a second light source configured to generate second light; and
a light detector disposed adjacent to the second light source and receiving the second light.

15. The biometric system of claim 14, wherein each of the first light source and the second light source comprises a light emitting device.

16. The biometric system of claim 11,
wherein the biometric device and the sensing device are alternately disposed in a first direction and in a second direction intersecting the first direction.

17. The biometric system of claim 11, further comprising a transparent cover connected to an edge of the substrate and covering the biometric device and the sensing device.

18. The biometric system of claim 11,
wherein the biometric device is provided in plurality,
wherein the plurality of biometric devices are disposed on two sides of the sensing device.

19. The biometric system of claim 18,
wherein the substrate is concavely bent so that the plurality of biometric devices come closer to each other.

* * * * *